United States Patent [19]
Sato et al.

[11] Patent Number: 5,541,851
[45] Date of Patent: Jul. 30, 1996

[54] METHOD AND APPARATUS FOR DISCRIMINATING CHEMICAL/PHYSICAL QUANTITY BASED ON THE TRANSIENT RESPONSE

[75] Inventors: Takaaki Sato; Junzo Hirono, both of Amagasaki, Japan

[73] Assignees: Agency of Industrial Science & Technology; Ministry of International Trade & Industry, both of Tokyo, Japan

[21] Appl. No.: 286,171

[22] Filed: Aug. 5, 1994

[30] Foreign Application Priority Data

Dec. 27, 1993 [JP] Japan ................................... 5-354237

[51] Int. Cl.⁶ ...................................................... G06G 7/75
[52] U.S. Cl. .......................... 364/497; 364/550; 73/23.21; 73/23.34; 73/865.7; 73/31.05
[58] Field of Search .......................... 364/550, 480–483, 364/496–499, 505–508, 524, 525, 558, 23.21; 73/23.34, 23.4, 24.06, 25.05, 31.05, 865.7; 257/443

[56] References Cited

U.S. PATENT DOCUMENTS

| | | | |
|---|---|---|---|
| 4,457,161 | 7/1984 | Iwanaga et al. | 73/31.05 |
| 4,498,004 | 2/1985 | Adolfsson et al. | 250/227.21 |
| 4,542,640 | 9/1985 | Clifford | 73/31.06 |
| 4,670,405 | 6/1987 | Stetter et al. | 436/151 |
| 4,818,348 | 4/1989 | Stetter | 205/780 |
| 4,888,295 | 12/1989 | Zaromb et al. | 436/161 |
| 5,177,805 | 1/1993 | Groger et al. | 385/12 |
| 5,214,388 | 5/1993 | Vranish et al. | 324/683 |
| 5,239,483 | 8/1993 | Weir | 364/497 |
| 5,373,452 | 12/1994 | Guha | 364/550 |
| 5,482,855 | 1/1996 | Yamafuji et al. | 435/287.1 |

OTHER PUBLICATIONS

Persaud et al, "Design Strategies for Gas and Odour Sensors," *IEE Colloq.* 1990, pp. 2/1–2/2.

Hart, "The artificial nose," *Chemistry and Industry*, No. 19, Oct. 2, 1989, pp. 620–622.

Primary Examiner—Emanuel T. Voeltz
Assistant Examiner—Kyle J. Choi
Attorney, Agent, or Firm—Oblon, Spivak, McClelland, Maier & Neustadt, P.C.

[57] ABSTRACT

A method for discriminating a chemical/physical quantity comprises exposing a sensor array consisting of a plurality of sensor members exhibiting differing response ranges with respect to a chemical/physical quantity to stimulation and discriminating the cause of the stimulation from the order in which the sensor members produce lowest significant (discriminable) output levels.

27 Claims, 6 Drawing Sheets c3: PROPIONIC ACID
c4: n-BUTYRIC ACID
c5: n-VALERIC ACID
c6: n-CAPROIC ACID
c7: n-HEPTYLIC ACID
c8: n-CAPRYLIC ACID
c9: n-PELARGONIC ACID a3: n-PROPYL ALCOHOL
a4: n-BUTYL ALCOHOL
a5: n-PENTYL ALCOHOL
a6: n-HEXYL ALCOHOL
a7: n-HEPTYL ALCOHOL
a8: n-OCTYL ALCOHOL
a9: n-NONYL ALCOHOL

METHOD AND APPARATUS FOR DISCRIMINATING CHEMICAL/PHYSICAL QUANTITY BASED ON THE TRANSIENT RESPONSE

BACKGROUND OF THE INVENTION

1 Field of the Invention

This invention relates to a discrimination method for analyzing and evaluating various chemical and physical quantities (hereinafter referred to as "chemical/physical quantities") including, for example, the species and nature of molecules whose chemical stimulation is sensed as odor or taste, the frequency band and quality of sound, and the wavelength band and color of light, and to an apparatus for conducting the method.

2 Description of the Prior Art

The conventional method of detecting and discriminating a chemical/physical quantity has consisted of setting up a plurality of sensors having differing sensitivities with respect to the respective components of the chemical/physical quantity, exposing the sensors to stimulation, waiting a prescribed period of time considered sufficient for the sensor outputs to reach and stabilize at higher than prescribed levels, and either deriving or comparing the sensor levels for evaluating the stimulation (chemical/physical quantity to which the sensors were exposed).

In a system for evaluating audible sound, for example, the incident stimulation (audible sound) has been analyzed and the sound quality evaluated by dividing the audible range (20–20,000 Hz) into $n$ number of frequency bands (where $n$ is a positive integer greater than 1) or into $n$ number of successive frequency bands whose center frequencies differ by one octave in the manner of 20 Hz, 40 Hz, 80 Hz, 160 Hz, 320 Hz . . . , setting up $n$ number of sensors each having the highest sensitivity in one of the respective bands or setting up $n$ number of acoustic sensors tuned to high Q values at the respective center frequencies (so as to exhibit sharp bandpass filter characteristics), deriving stable transduced voltages (currents) from the sensors, and determining the sound pressures of the individual frequency components of the incident stimulation (audible sound). The measurement resolution and the evaluation accuracy increase with the number of divisions $n$.

Color and light have been evaluated in a similar manner. Specifically, the analysis and evaluation has been conducted by dividing the light wavelength range into $n$ number of bands, using n number of photoelectric converters each having high sensitivity in one of the bands as sensors serving as bandpass filters with differing center frequencies, and using the light intensity information obtained after the sensor outputs have stabilized as the basis for determining the intensity of the respective frequency components of the incident stimulation (light or color).

Basically the same method has also been used for other physical and chemical quantities. Even odor and taste, traditionally considered to be peculiar to living organisms, have become the target of intensive research into ways for analyzing and discriminating stimulation by electrical and electronic means. Published reports regarding odorants include, for example, *Nature,* 1982, Vol. 299,352–355 (Ref. no. 1); *Nikkei Science,* October 1991, 68–76 (Ref. no. 2), and T.IEE Japan, 1993, Vol. C 113, 621–626 (Ref. no. 3). In each of these earlier reports, however, the sensor outputs are derived and evaluated after the output values of the sensors have become greater than a prescribed level.

As will be understood from the foregoing, the prior art method of evaluating chemical/physical quantities is time consuming because the constituents of the chemical/physical quantity can be derived and the chemical/physical quantity be evaluated only after the sensor outputs have stabilized. Depending on the type of stimulation to be evaluated, the time required for the sensor outputs to stabilize may be very long.

Another problem of the prior art method is that measurement frequently becomes impossible when the incident stimulation is intense because the sensor outputs saturate before the end of the measurement period.

This invention was accomplished in response to the foregoing circumstances and has as its object to provide a method and apparatus for discriminating a chemical/physical quantity that enable the chemical/physical quantity analysis and evaluation to be conducted at high speed without degradation of evaluation capability owing to sensor saturation.

SUMMARY OF THE INVENTION

For achieving the aforesaid object, this invention provides a method for discriminating a chemical/physical quantity comprising the steps of exposing a sensor array consisting of a plurality of sensor members exhibiting differing response ranges with respect to a chemical/physical quantity to be discriminated to stimulation and discriminating a stimulation component of the chemical/physical quantity from the order in which the sensor members produce lowest significant (discriminable) output levels.

Thus in this invention the chemical/physical quantity is not discriminated using a value whose magnitude corresponds to the incident stimulation intensity after the output of the sensor exposed to the stimulation has stabilized but using a dynamic response characteristic exhibited by the sensor in the course of rising to said value, particularly in the initial period of the rise. The invention is therefore able to discriminate chemical/physical quantities accurately at high speed.

In addition, the invention can discriminate a chemical/physical quantity based not only on the order in which the sensor members produce the lowest significant output levels but also on differences in sensor output level response characteristics between the sensor member which is first to produce a lowest significant output level and sensor members which are second and later to produce a lowest significant output level.

The invention can further calculate the stimulation intensity of a chemical/physical quantity on the basis of a transient output level rise period dynamic characteristic, for example the output level rise rate, of the sensor member which is first to produce a lowest significant output level.

The above and other objects, characteristic features and advantages of this invention will become apparent to those skilled in the art from the description of the invention given hereinbelow with reference to the accompanying drawings.

DESCRIPTION OF THE PREFERRED EMBODIMENTS

Figure 1:
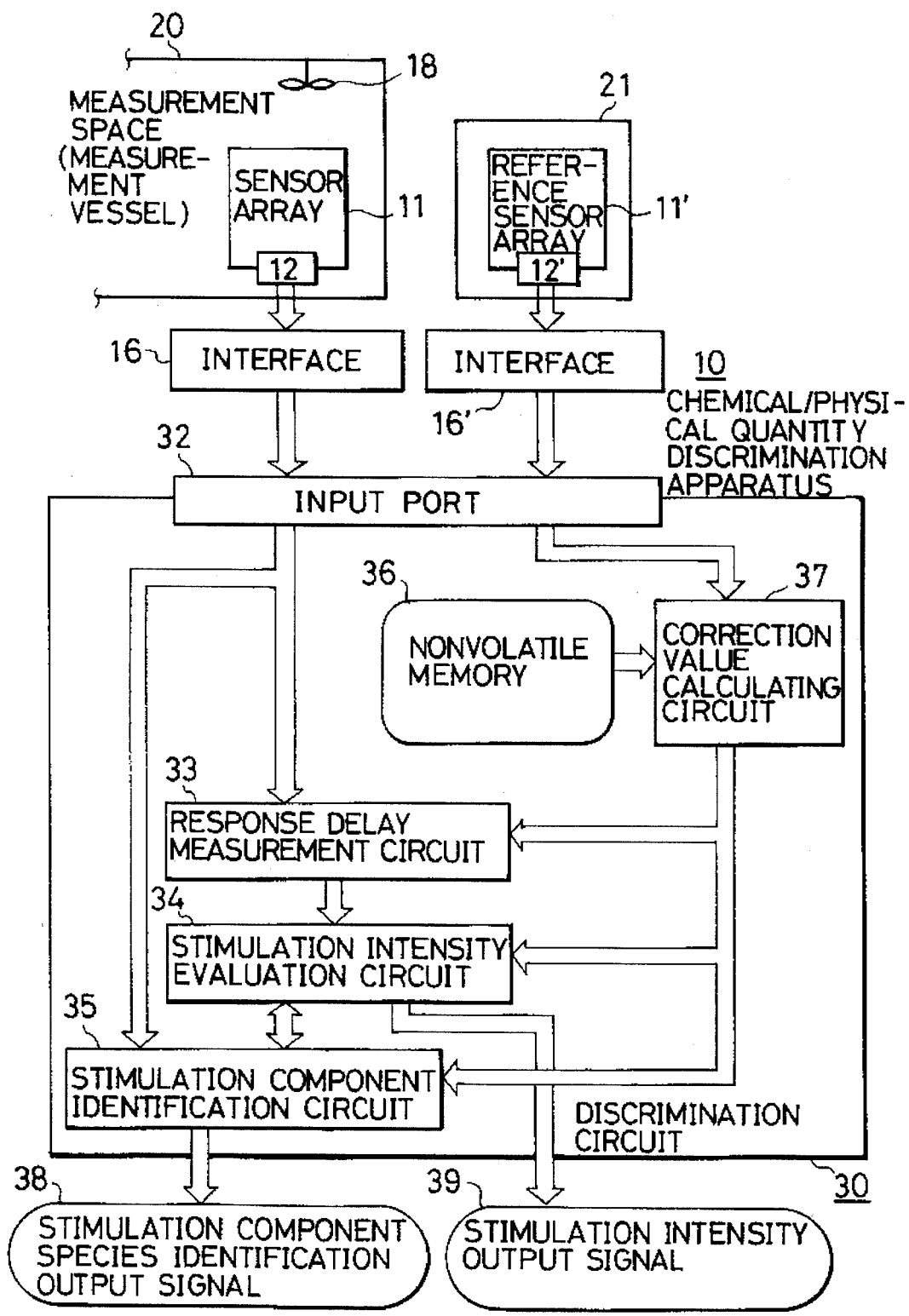
FIG. 1 is a schematic view showing the configuration of an embodiment of the apparatus for discriminating a chemical/physical quantity according to the invention.

FIG. 1 shows the general configuration of a chemical/ physical quantity discrimination apparatus 10 which is an embodiment of this invention. The apparatus 10 consists of two major sections: a sensor array 11 disposed in a measurement space (or measurement vessel) 20 in which the chemical/physical quantity to be evaluated is present and a discrimination circuit 30 for processing the signals output by the sensor array 11. The discrimination circuit 30 includes functional circuits 33, 34, 35 and 37 for performing required processing functions to be described below and a memory 36 for storing various kinds of data explained later. While some or all of the circuits 33, 34, 35 and 37 can be constituted using dedicated hardware, the functions required of the individual functional circuits can also be realized by programming a computer. The memory 36 can be an internal computer memory or, if sufficient capacity cannot be secured internally, can be an external memory.

Figure 2A:
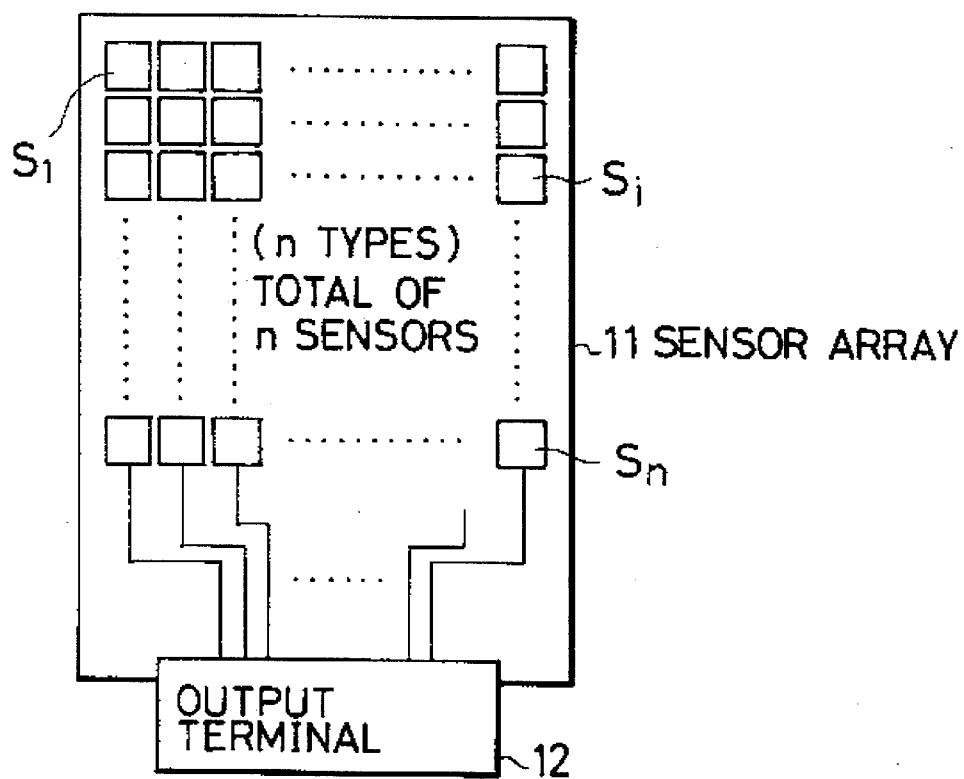
FIG. 2(A) is an explanatory view showing details of the sensor array of the apparatus of FIG. 1.
Figure 2C:
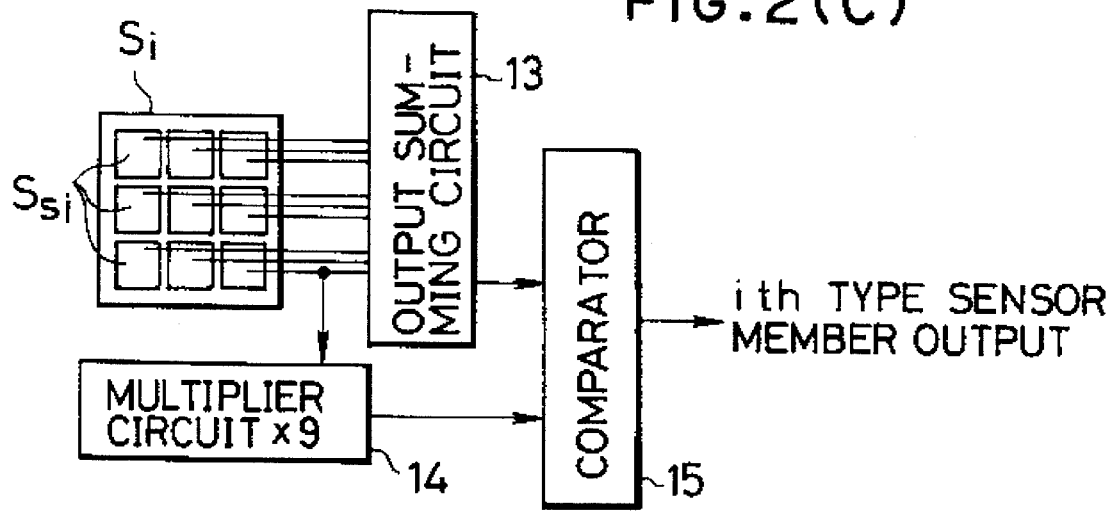
FIG. 2(C) is an explanatory view showing one sensor member of the sensor array of FIG. 2(A).
Figure 2B:
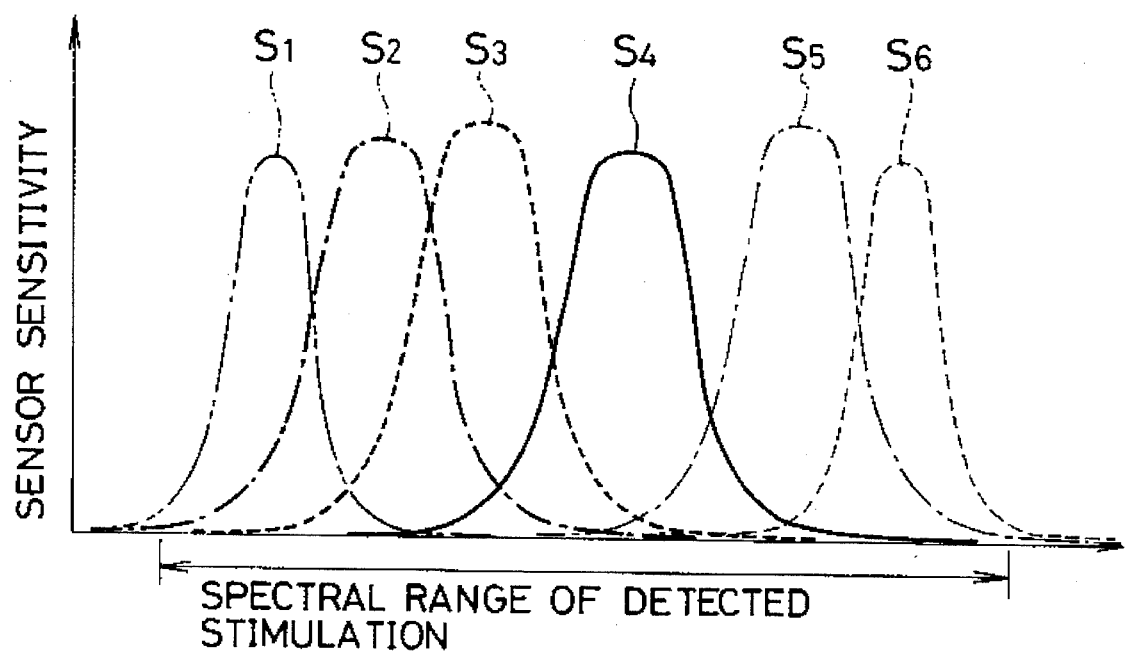
FIG. 2(B) is a graph showing the stimulation spectral range when the array is constituted of a plurality of sensors whose sensitivities exhibit differing response ranges.

In this invention, the overall extent of the chemical/ physical quantity to be discriminated is divided into $\underline{n}$ number of ranges, where $\underline{n}$ is an integer greater than one. The ranges can overlap slightly or can be totally discrete. In this specification, the components of the chemical/physical quantities within the subdivided regions are referred to as "stimulation units." In correspondence to the subdivided ranges, a total of $\underline{n}$ sensor members Si ($i = 1, 2, 3, \ldots, n$) of $\underline{n}$ types having mutually differing sensitivities with respect to the stimulation units $\underline{i}$ ($1 \leq i \leq n$) are arranged to form the sensor array 11 as shown in FIG. 2(A). While FIG. 2(A) shows the sensor members Si arranged in rows and columns, various other geometric arrangements can also be used. FIG. 2(B) is a graph showing stimulation spectral range of the individual sensors and the stimulation spectral range of the array in the case where the array is constituted of six sensors S1–S6 exhibiting differing response ranges with respect to six stimulation units. FIG. 2C(B) shows a case in which each ith type sensor member Si between the 1st type and the nth type is constituted of a plurality of sensors Ssi. This will be explained later.

The output of each sensor member Si is forwarded to the discrimination circuit 30 through an output terminal 12 provided on the sensor array 11 and an input port 32 of the discrimination circuit 30 shown in FIG. 1. This signal transmission path is provided at an intermediate point with an interface 16 suitable for the sensors actually used in the sensor members Si. The interface 16 is, for example, an amplifier for optimum low-noise amplification of weak sensor outputs or a buffer for input-output impedance matching. If the sensor members Si produce analog signals and the discrimination circuit 30 is designed to process digital signals but does not include an internal A/D converter, the required A/D converter can be built into the interface 16 as an external unit. On the other hand, if the sensor members Si do not output current or voltage signals over wires but transmit their signals from antennas or output magnetic or optical signals, the interface 16 can include a receiver. In any case, the signals from the sensor members Si or the sensor array 11 are sent to the discrimination circuit 30, which serves as the signal processing unit. Various prior art circuits can be incorporated into the interface 16 of FIG. 1 as desired for processing the transmitted signals into the proper type and magnitude for processing in the discrimination circuit 30. If, as is seen in the case of electret condenser microphones, for example, the sensor members Si have to be supplied with electric power, they can be connected with a power supply (not shown) by providing the required power input terminals in the section indicated as the output terminal 12 in FIG. 1 and FIG. 2(A) and running power wires to the respective sensors.

Figure 3A:
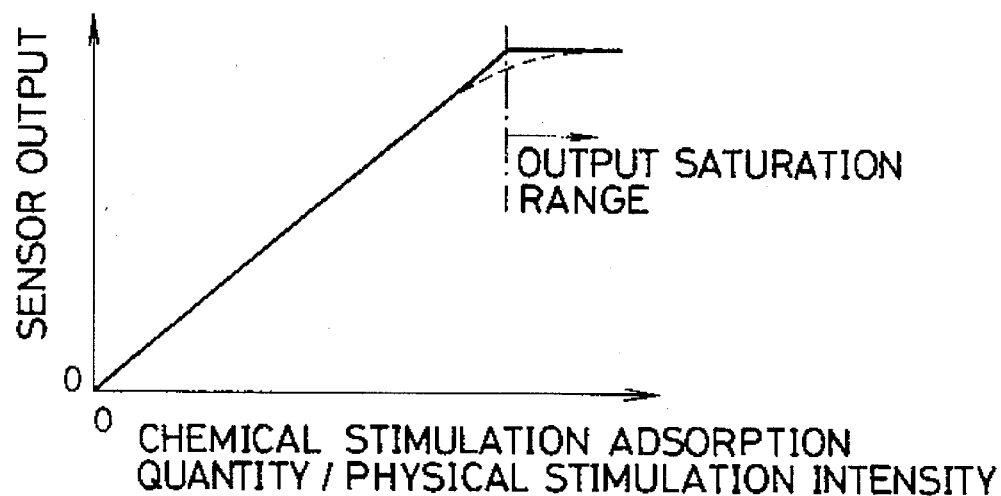
FIG. 3(A) is a graph showing how sensor output varies with stimulant concentration.

For simplicity, the principle of the invention will first be explained in general, basic terms regarding sensor outputs common to all types of sensors. As shown in FIG. 3(A), in the case of both chemical stimulation and physical stimulation, the sensor output in the non-saturated sensor output region is proportional to the stimulation intensity (which is equal to the chemical adsorption quantity in the case of chemical stimulation and to the stimulation intensity itself in the case of physical stimulation) acting on the sensing surface of the sensor. As the output approaches the output saturation region, the relationship may deviate from linearity as in the typical example shown by the phantom line in FIG. 3(A). Particularly in the case of chemical stimulation, moreover, the information which is desired from the sensor output is generally not the chemical adsorption quantity but the stimulant concentration. The relationship between the adsorption quantity and the stimulant concentration may be based on either of two types of interaction between the stimulant and the sensing service: specific adsorption or nonspecific adsorption.

When it is based on nonspecific adsorption, and in the absence of saturation, the relationship between the stimulation concentration and the adsorption quantity maintains the proportional relationship defined by Gibbs adsorption equation. In this case, therefore, the characteristic of FIG. 3(A) can be defined as the relationship between the stimulant concentration and the sensor output. At any rate, insofar as a linear relationship holds, the linear equation and its proportionality coefficient can be easily determined by pretesting each of the sensor members Si actually used in the sensor array 11. The so-determined arithmetic expression or the corresponding algorithm or proportionality coefficient can then be stored in the ROM or other nonvolatile memory 36 of the discrimination circuit 30 shown in FIG. 1. In the simplest case, once the proportionality coefficient has been stored in memory, it generally suffices to establish the arithmetic expression in the form of hardware circuitry or, if a computer is used, to program it into the computer.

As mentioned earlier, a computer can be programmed to provide the functions of the discrimination circuit 30. The memory for storing the computer program is not shown in the drawing because it is universally known that a computer system has a memory for programs. In other words, the matter of how the ordinary means possessed by a computer system are used for realizing the embodiments of the invention described in this specification is essentially one that can be decided on the basis of design considerations by a person skilled in the art.

Figure 3B:
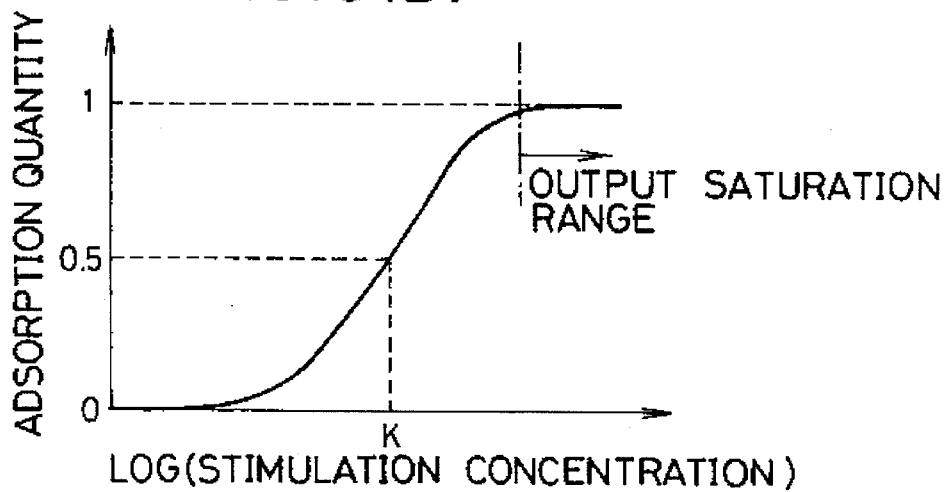
FIG. 3(B) is a graph showing how stimulation adsorption quantity varies with stimulation concentration.

When it is based on specific adsorption, on the other hand, the relationship between the stimulation concentration C and the adsorption quantity B(C) becomes a Michaelis-Menten type nonlinear one, as shown in FIG. 3(B), and can be expressed as $$B(C) = \alpha \times (C/K)/\{1+(c/k)\} \qquad (1)$$

where K is the dissociation constant and $\alpha$ is the proportionality coefficient.

Even in this case, however, if the stimulation concentration is smaller than the dissociation constant by one order of ten or more, i.e. at a low concentration of $C<(K/10)$, the denominator of Eq. (1) can be approximated as 1, making it possible rewrite Eq. (1) as $$B(C) = \{\alpha \times (C/K)\} \propto C \qquad (2)$$

When the stimulation intensity is low, therefore, it becomes possible, irrespective of whether the type of stimulation is chemical or physical, to calculate the stimulation intensity merely by multiplying the output levels corresponding to the stimulation intensities obtained from the sensor members Si by the proportionality coefficient. Thus, similarly to what was explained earlier regarding the linear relationship, if the proportionality coefficient is stored in the memory 36 of the discrimination circuit 30 shown in FIG. 1, the stimulation intensity can be readily calculated by multiplying the output level information obtained from the sensor members Si through the input port 32 by the proportionality coefficient in a stimulation intensity evaluation circuit 34. Otherwise, if necessary, the stimulation intensity evaluation circuit 34 can calculate the stimulation intensity from the more accurate specific adsorption relationship expressed by Eq. (1).

A new concept of the present invention will now be discussed in its relationship to the intensity $f$ of the incident unit stimulations $i$ and the initial response characteristics of the sensor members Si, namely the transient dynamic characteristics from the time the stimulation is received. For the purpose of this discussion it will be assumed that in a sensor member whose output level is increasing under exposure to stimulation the incident intensity $f$ does not vary during the time required for the output level to reach a value sufficiently close to that corresponding to the intensity $f$ (for example, 70% or more of the value corresponding to the stimulation intensity). In the case of a physical stimulation, this condition is generally satisfied almost automatically, even without implementing any particular measures, owing to the adequately fast sensor response. In contrast, in the case of a chemical stimulation, the condition is not necessarily satisfied and, therefore, as a countermeasure in the case that the sensor response speed is unacceptably slow, it is possible for instance to sample a prescribed amount of the chemical/physical quantity to be discriminated and seal the sample in a closed space including the sensor array while the sensor array is conducting the measurement. When the condition has been satisfied, by whatever means, the sensor output will rise from zero at a fixed rate in the case of a physical stimulation (see FIG. 3(C)). Since the sensor output during initial response is proportional to the value of the stimulation intensity integrated over the stimulation exposure time (interaction time), the rate at which it rises increases in proportion to the stimulation intensity $f$. In the case of a chemical stimulation, on the other hand, only the increase in adsorption quantity under a prescribed concentration need be considered and, therefore, a sensor output can be obtained which starts from zero before exposure to the stimulation and then, after exposure, rises at a rate proportional to the final adsorption quantity.

Figure 3C:
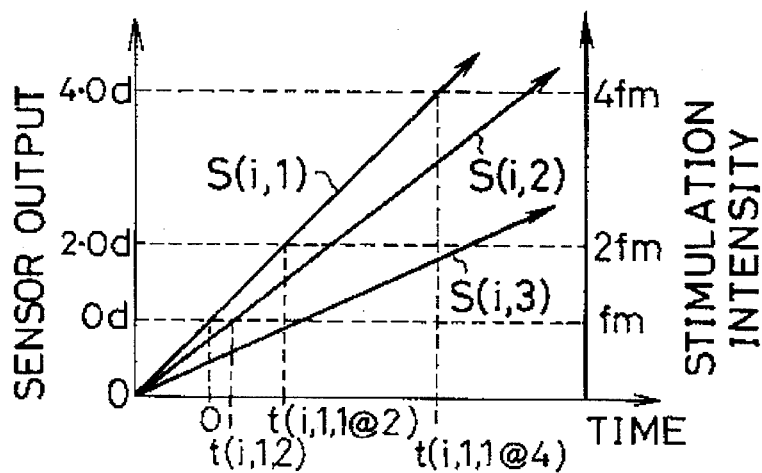
FIG. 3(C) is a graph showing how sensor output varies with stimulation intensity.

As a result, the sensor output is linear as shown in FIG. 3(C) for both physical and chemical stimulations and, moreover, the rise rate (slope of the linear equation defining the linear relationship) of the sensor member S(i,1) with highest sensitivity with respect to the incident unit stimulation $i$ is greater than that of the sensor member S(i,2) with the second highest sensitivity, which is greater than that of the sensor member S(i,3) with the third highest sensitivity, and so on for sensor members with progressively lower sensitivities.

Consideration will therefore be given to the case where the sensor array 11 of the apparatus 10 shown in FIG. 1 is exposed to a given unit stimulation $i$ within the chemical/physical quantity to be evaluated (which case can be considered equivalent to one in which the chemical/physical quantity consists of only a single unit stimulation $i$). Define the stimulation intensity of the incident unit stimulation $i$ as $f$. Then, for the reason explained with reference to FIGS. 3(A), (B) and (C), a finite period of time of fairly long duration is required for the detection outputs of the sensors Si to rise from zero to levels corresponding to the incident intensity $f$. As was also explained earlier, however, when the initial response period outputs of the sensor members Si are observed, it is found that the integrated stimulation intensity value increases monotonously with respect to time. Therefore, the first among all of the sensor members S1–Sn to reach a discriminable (significant) output level Od (the lowest significant output level) is the sensor member S(i,1) having the highest sensitivity with respect to the incident unit stimulation $i$. As also shown in FIG. 3(C), the time point at which this occurs is the calculation origin point "0" on the time axis for the discrimination processing in the embodiment under discussion. The next sensor member to produce a significant output signal level Od is the sensor member S(i,2) with the second highest sensitivity with respect to the unit stimulation $i$.

The difference between the times at which sensor member S(i,1) and the sensor member S(i,2) reach the significant output level Od (the corresponding stimulation intensities are indicated in terms of intensity component fm in FIG. 3(C)) is peculiar to the incident unit stimulation $i$. In an actual application of the apparatus according to the invention, however, there is no way of knowing the instant at which the sensor array 11 is exposed to the unit stimulation $i$. The response time difference is therefore calculated as a time from the time calculation origin point in the following modified manner.

As was explained earlier and will be easily understood from FIG. 3(C), the time at which one of the sensor members S(i,1) of the sensor array 11 (ordinarily the sensor member with the highest sensitivity with respect to the incident unit stimulation $i$) first produces a significant output level Od distinguishable from the background noise is defined as the time calculation origin point "0". Defining the time difference between this time point and the time at which another sensor member S(i,2) (the sensor member having the second highest sensitivity with respect to the incident unit stimulation $i$) produces an output level Od of the same value as t(i,1,2) and the time required for the highest sensitivity sensor member S(i,1) that responded first to produce an output level twice that of the aforesaid output level Od (2×Od) as t(i,2,1@2), and calculating the ratio Rt(i,1,2) between these times as $$Rt(i,1,2)=t(i,1,2)/t(i,1,1@2) \quad (3)$$

there is obtained a value of Rt(i,1,2) peculiar to the incident unit stimulation $\underline{i}$.

Thus the incident-unit stimulation $\underline{i}$ can be readily determined from information obtained by monitoring the outputs of $\underline{n}$ number and $\underline{n}$ types of sensor members Si to determine the order {S(i,j): j=1,2 . . . , n} in which they produce the output level Od and by calculating the rated response delay data {Rt(i,1,j): j=1,2 . . . , n} of the individual sensors. Since the sensor members having substantially no sensitivity with respect to the incident unit stimulation $\underline{i}$ do not produce significant outputs, the number of responding sensors will differ considerably between different unit stimulations $\underline{i}$ and in some cases may be only one.

The mechanism of the invention will now be explained in detail with reference to FIG. 1. In the case where a stimulation X incident on the sensor array 11 disposed in the measurement space or measurement vessel 20 consists of a single unit stimulation $\underline{i}$ (=X) and only one sensor produces a significant (discriminable) output level Od within a prescribed time period, the incident stimulation X can be identified as the specific single stimulation unit among the group of stimulation units for which the sensor S(X,1) exhibits the highest sensitivity. If the fact that the sensor S(X,1) is a "specific" sensor which responds only to the stimulation $\underline{i}$ has in advance been stored as known standard response pattern information in the memory 36 constituting one circuit element of a stimulation component identification circuit 35, the stimulation component identification circuit 35 can, by reading the stored data and ascertaining the correspondence, immediately discriminate that the incident chemical/physical quantity is of the type wherein the unit stimulation $\underline{i}$ equals X and output a stimulation component species identification output signal 38.

In other words, if a total of $\underline{n}$ sensors are used such that for each of the $\underline{n}$ regions into which each of the unit stimulations $\underline{i}$ are divided there is one "specific" sensor exhibiting the highest sensitivity with respect to that region, the stimulation component identification circuit 35 can determine the sensor S(X,1) which output the largest signal by comparing the responses of the $\underline{n}$ sensors, whereby the incident unit stimulation $\underline{i}$ can be simply and immediately determined. In this specification, the word "specific" as termed with respect to a sensor means "having the highest sensitivity," in other words "able to achieve identification with respect to a unit stimulation group at the lowest stimulation intensity." This does not preclude the possibility that two or more sensors may respond when the stimulation intensity is high. The broader the stimulation intensity range over which sensors maintain their specificity, the easier it is to identify the unit stimulations constituting the stimulation. Although this invention requires a certain amount of time for ascertaining the response of a single sensor S(X,1), the length of this time is kept short by utilizing the output state of the sensors during their initial response period, and, in particular, is much shorter than the time required by the prior art method in which reading of the sensor output has to be delayed until the output has completely stabilized.

When, differently from the foregoing, one or more other sensors Si also respond to the unit stimulation $\underline{i}$ in addition to the single sensor S(X,1), the basic data associated with sensor S(X,1), the first sensor to respond, is read from among the standard response patterns stored in the memory 36 so as to obtain a group of candidate unit stimulations $\underline{i}$. The stimulation component identification circuit 35 then detects the sensor S(i,2), the second sensor to respond, and a response delay measurement circuit 33 calculates Rt(i,1,2) using Eq. (3). By using the calculated response delay data Rt(i,1,2), the group of candidate stimulation units can then be reduced to a small number. If a comparison with the group of associated basic data of the standard response patterns stored in the memory 36 still does not enable identification of a single stimulation unit, the third sensor to respond, the sensor S(i,3), is detected and Rt(i,1,3) is calculated by replacing t(i,1,2) in Eq. (3) with t(i,1,3), whereafter the same procedure is repeated in order for later responding sensors until unit stimulation $\underline{i}$=X is determined.

The calculation or estimation of the stimulation intensity of the incident stimulation X can be explained as follows. As was mentioned earlier, the sensor output should be proportional to the stimulation intensity $\underline{f}$ when the stimulation intensity is weak. Further, the output rise rate during the transient period from the zero output level state immediately before the sensors Si are exposed to the stimulation (while the fact that a level offset may arise with some kinds of sensors is ignored in this specification, this does not detract from the generality of the explanation) to the time when the output reaches the maximum for the incident stimulation intensity, particularly the output rise rate during the initial response period, can, as explained earlier with reference to FIG. 3(C), be assumed to be directly proportional to the intensity of the incident stimulation. The apparatus 10 of this embodiment adopts this assumption and the data relating to the associated proportionality coefficients is stored in the memory 36 used for storing various types of basic data. The stimulation intensity evaluation circuit 34 can therefore easily calculate the intensity $\underline{f}$ from the time data (rise rate data) t(i,1,1@2) relating to the output level of the sensor member Si concerned and the proportionality coefficient data stored in the memory 36 If greater measurement precision is desired, the calculation is based on two values by including the time t(i,1,1@4) required for the output of the sensor member concerned to reach 4×Od or on three values by further including the time t(i,1,1@8) required for the output level to reach 8×Od.

An explanation will now be given regarding discrimination of a stimulation Y consisting of a stimulation unit group having m(m>1) stimulation elements. This is representative of the most generally observed situation. As was explained earlier, when each of the sensors has a "specific" high sensitivity region extending over an order of ten or more with respect to the stimulation intensity of a specific unit stimulation $\underline{i}$, then, for the reason also explained earlier, it is relatively easy to achieve identification with respect to the stimulation unit group. The main component y1 of the stimulant Y can be identified from S(y,1) which can be found by the stimulation intensity evaluation circuit 34. In particular, if the stimulation component identification circuit 35 and the stimulation intensity evaluation circuit 34 are able to detect that the output of S(Y,1) is increasing monotonously or is maintaining a substantially constant value, then, at the time that this state is detected, the stimulation intensity evaluation circuit 34 will ascertain that the stimulation intensity is $\underline{f}$ and output this information as a stimulation intensity output signal 39 which, in combination with the stimulation component species identification output signal 38, make it, possible to obtain the information that the stimulation component y1 is present at the intensity $\underline{f}$.

This will be explained in more detail. In a situation like the one discussed above, the effect on the output of the sensor S(Y,1) by another component whose contribution in terms of stimulation intensity is an order of ten or more smaller than the stimulation component y1 can, with rare exception, be considered negligible. It therefore follows that the value of f'(y1) calculated in the stimulation intensity evaluation circuit 34 from the time data t(i,1,1@2), namely the rise rate data, and the aforesaid proportionality coefficient will be in good agreement with the actual stimulation intensity f(y1) of the stimulation component y1. For improving the measurement accuracy, components whose contributions to the stimulation rank second or lower should best be corrected in light of the effect that components whose contributions are larger than these components have on the output of the sensor member concerned. Such basic data can be easily obtained beforehand for at least down to the third component level. By in advance storing the data in the memory 36 as part of the known standard response pattern, it becomes possible to conduct the correction using the stored information.

For enabling the method of this invention to be conducted with high accuracy it is preferable to further implement certain measures with respect to the apparatus fabricated to carry out the method as well as to the site where the method is conducted. One of these is to use sensors with the lowest noise level possible. This is preferable from the viewpoint of minimizing the measurement time and improving the measurement accuracy results, which improve as the lowest significant (discriminable) output level Od becomes smaller.

It is also preferable for the sensing surfaces of all $\underline{n}$ number of sensor S1-Sn to be exposed to the stimulation simultaneously and uniformly. For achieving this, the volume of the measurement space or measurement vessel 20 should be made small and the sensor members should be disposed in close proximity. Especially in the case of a chemical stimulation, it is advisable to provide a fan or stirrer 18 (FIG. 1) or like active agitation means in the measurement space or measurement vessel 20 and to use this means to conduct forced stirring. If, despite this expedient, the time required for the concentration at the sensor members to reach uniformity is still so long that variation in stimulation intensity becomes a problem, the problem can be coped with by calculating the average sensor output rise rate over a prolonged period, e.g. over a period equal to about one-half the stimulation exposure time, and using the calculated value for calculating the stimulation intensity.

Similarly, in implementing the invention it is preferable for the sensor members to respond to stimulation exposure by rising from the level at no stimulation to a prescribed level with good reproducibility. This can be best ensured by intermittently exposing the sensing surfaces to stimulation, namely by repeatedly alternating stimulation exposure periods and stimulation exposure rest periods. The stimulation exposure rest periods can be produced by discontinuing the stimulation, removing the chemical substance or otherwise forcibly establishing a stimulation-free state. The stimulation exposure rest periods can be of fixed length or can be continued up to the point that the monitored sensor output assumes the same level as in the stimulation-free state. When fixed rest periods are used they are preferably established to be sufficiently long for the outputs of the sensor members to fall back to within the range where the sensor member outputs rise linearly relative to time passed from the start of stimulation exposure and should be between one and two times the length of the stimulation exposure periods. In this case it is preferable to carry out a correction by subtracting the sensor output at the end of a rest period from the sensor output during the following stimulation exposure period. Separate circuits for conducting these operations are not shown in FIG. 1 but the required circuitry can be incorporated in the discrimination circuit 30. Such correction can, for example, be conducted by the stimulation component identification circuit 35 and the stimulation intensity evaluation circuit 34.

Where the aforesaid stimulation exposure rest periods have been implemented but it is desired to conduct the measurement in an even more intermittent manner, this can be achieved by disposing a plurality of sensor arrays 11, . . . for joint exposure to the chemical/physical quantity to be discriminated, arranging for some of the sensor arrays 11 to be exposed to stimulation while the other sensor arrays 11 are in their stimulation exposure rest period, and conducting the aforesaid discrimination operations on the basis of the signals successively obtained in time series from the sensor arrays 11 exposed to the stimulation. In principle, it is possible to use a plurality of the apparatuses 10 shown in FIG. 1, dispose their sensor arrays for exposure to the chemical/physical quantity to be discriminated, and conduct the same processing as that conducted with respect to the aforementioned plurality of sensor arrays. In this case, there is of course provided an apparatus (which can be a computer) for integrally interpreting and processing the discrimination signals produced by the plurality of apparatuses 10.

As a way of enhancing the reliability and signal-to-noise ratio (S/N) of the output level signals produced by the individual sensors Si within the sensor array 11 it is effective, as shown in FIG. 2, to constitute each ith type sensor Si of a set of like type sensor elements Ssi and carry out correction in view of their outputs. For example, the sensor Si shown in FIG. 2(C) is constituted of nine same type sensors Ssi disposed in close proximity. The outputs of all nine sensors are forwarded to a output summing circuit 13 while the output of one sensor Ssi is increased nine times by a multiplier 14. The outputs of the output summing circuit 13 and the multiplier 14 are forwarded to a comparator 15 which compares them and outputs an ith type sensor member output to the discrimination circuit 30. This arrangement greatly increases the ability to distinguish whether minute electric signals produced by the sensor members are actually significant signal components and not noise components. The circuits 13 and 14 and the comparator 15 can be provided either on the sensor array 11 side or on the discrimination circuit 30 side. In the latter case the number of signal transmission lines becomes considerable if parallel transmission is used. Where the discrimination circuit 30 is constituted as a computer, therefore, it is preferable to cope with any limitation on the number of computer input ports by inputting the sensor Si or sensor element Ssi signals using time-shared serial input instead of parallel input. This is an ordinary technique that is well known in the computer field and can be implemented by those skilled in the art as required.

Further, as additionally shown in FIG. 1, correction data can also be obtained by providing a reference sensor array 11' in a stimulation-free space 21 isolated from the effect of the stimulation. When a plurality of sensor arrays 11 or apparatuses 10 are used as explained earlier, each of them is equipped with a similar reference sensor array 11' configured in exactly the same way as the sensor array 11. Thus the configuration of the reference sensor array 11' can be represented by adding primes to the reference symbols in FIGS. 2(A) and 2(C). Likewise, the interface 16' is identical to the interface 16. Thus, while interface 16' is shown to be independent of the interface 16 in FIG. 1, interface 16 can provide the functions of both interfaces (by time sharing if necessary).

When the reference sensor array 11' is provided in this way so as not to be exposed to stimulation, the output levels produced by its sensor members can be used as correction or calibration values. This can be achieved and a system with higher discrimination accuracy realized by, for example, defining the output levels of the reference sensor array 11' sensors as reference outputs during no stimulation, comparing these reference outputs with the no-stimulation signal levels stored in the memory 36 to obtain the ratio or difference between them, having a correction value calculating circuit 37 calculate a correction coefficient from the ratio or difference, and correcting the sensitivity or output level of each of the sensors Si of the sensor array 11 exposed to stimulation for changes caused by temperature or ageing.

As was mentioned earlier, an offset may arise with some kinds of sensors. In such a case, it is possible to correct for the offsets and ensure the significance of all the derived signal levels simply by subtracting the output levels of the sensor members of the reference sensor array 11' from the corresponding sensor member output levels of the sensor array 11 exposed to stimulation. In conducting the aforesaid correction for changes caused by temperature or ageing it is preferable to conduct the aforesaid correction procedures based on the output levels obtained from the reference sensor array 11' intermittently at prescribed time intervals during the measurement period. From the viewpoint of the practical level, however, there is no particular need to adopt a statistical method of this type. This is because, as in the aforementioned offset correction, it is possible to obtain a signal level that can be treated as a corrected significant signal level simply by subtracting the sensor member output levels obtained from the reference sensor array 11' from the corresponding output levels obtained from the sensor array 11. Any of various other data correction techniques utilized in the prior art measurement technologies can also be adopted insofar as they are appropriate in view of the principle of the invention.

While the invention has been described with respect to one of its embodiments, it is not limited to this embodiment and can be freely modified within the scope of the claims as desired in light of design considerations. The mode in which the stimulation component species identification output signals 38 and the stimulation intensity output signals 39 are utilized can be freely selected. They can be made available for various studies by visually displaying them on an appropriate display, recording them on an appropriate recording medium or printing them out on paper with an appropriate printing device. In addition, the apparatus according to the invention can be incorporated in a monitoring apparatus or robot, for example, and the outputs signals be used directly as control signals for the monitoring apparatus or robot.

In the embodiment described in the foregoing, the point of time deemed to be the time calculation origin point in the response delay measurement circuit 33 etc. is that at which one among the $n$ number of sensors produces the first lowest significant output level $0d$ distinguishable from the noise level. Instead, however, it is possible to define an output level slightly higher than said lowest output level as the lowest significant output level $Od$ and to define the time calculation origin point as the point of time at which the output of one of the sensors exceeds this level.

The invention is not in principle limited as regards the chemical/physical quantities to which it can be applied, which is to say that any of the various prior art sensors can be used in the sensor members of the apparatus according to the invention. As was mentioned earlier, in the case of using acoustic sensors (which can generally be constituted as microphones), acoustic sensor members specific to individual ones of the $n$ number of ranges into which the chemical/physical quantity is divided (i.e. the individual stimulation units) can be easily configured by connecting each with a sharp bandpass filter or tuning filter exhibiting a high Q value at the center frequency of the corresponding unit stimulation. Similarly, in the case of using optical sensors, a group of sensors that can be called "specific" can be obtained by passing the electric signals converted from light by the respective optical sensors through bandpass filters exhibiting appropriately sharp bandpass characteristics at the respective center frequencies of subdivided ranges defined by, for example, dividing the 800 nm–900 nm wavelength region into 20 nm segments. If necessary, the sensing surfaces of the optical detectors can be fitted with auxiliary optical filters. In addition, sensors for other physical quantities, for example sensors for detecting stress-related quantities such as mechanical vibration frequency, tension period or compression period at a short cycle period, tensile strength, or compression strength, can also be used in this invention.

Figure 4A:
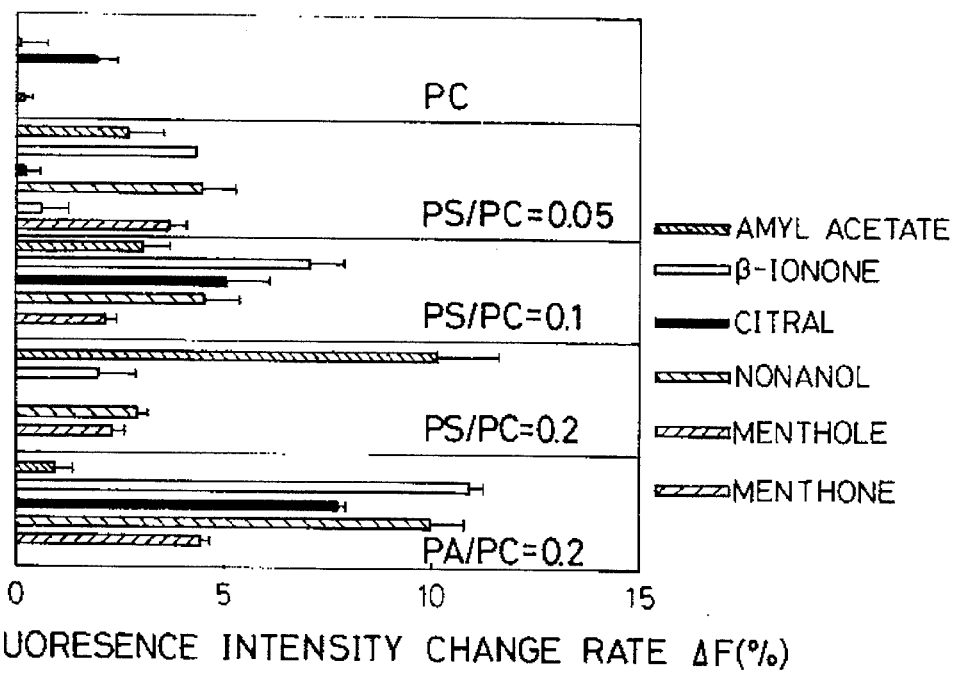
FIG. 4(A) is a graph showing how adsorption of odorants on liposomes varies with lipid composition.

It was previously thought difficult for electronic or electrical sensors to imitate the sensing capabilities long considered peculiar to living organisms. Now, however, sensors using lipid membranes have been developed which exhibit high sensitivity with respect to sour taste, salty taste, bitter taste, sweet taste and umami taste (see Ref. no. 1 mentioned earlier), and these sensors can also be used in this invention. Although no sensors with high specificity to odorants have been developed yet, it is highly like that at least some of the many ongoing research projects aimed at the development of such sensors will produce results in the near future. As shown in FIG. 4(A), lipid compositions and the like capable of varying the adsorptivity of odorants on liposomes have been discovered. In the graph of FIG. 4(A), the horizontal axis represents the rate of change $\Delta F(\%)$ in fluorescence intensity of fluorescence dyes adsorbed on liposomes. The graph shows the selectivity with respect to the odorants listed at the right of the graph (stimulation concentration of $10^{-6}M$) when PC (phosphatidylcholine), PS (phosphatidylserine) and PA (phosphatidic acid) were used as liposomes in five combinations (PC, PC/PC=0.05, PC/PC=0.1, PS/PC=0.2, PA/PC=0.1).

Figure 4B:
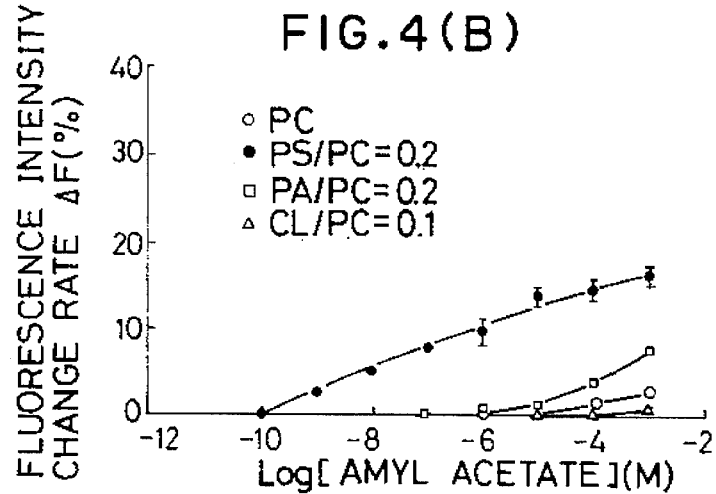
FIG. 4(B) is a graph showing the concentration dependency of sensor response to amyl acetate.
Figure 4C:
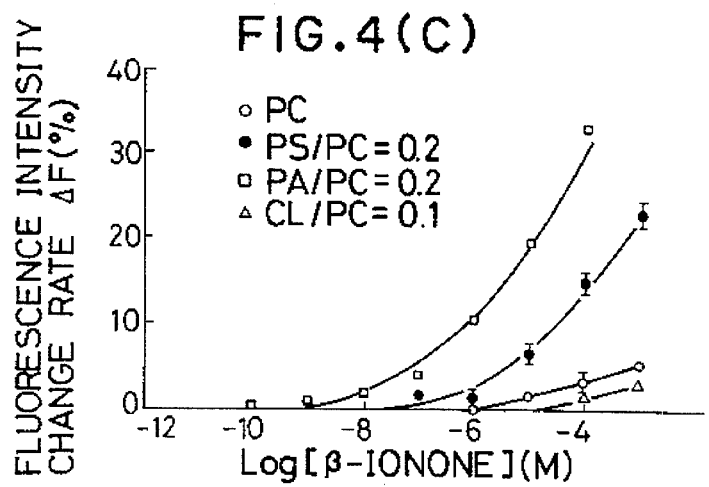
FIG. 4(C) is a graph showing the concentration dependency of sensor response to $\beta$-ionone.

In addition, the concentration dependence of the response of each odor sensor with respect to the odorant isoamyl acetate is shown in FIG. 4(B) and that for the odorant β-ionone is shown in FIG. 4(C). These results demonstrate the feasibility of combining lipid membranes to develop sensors with a certain degree of selectivity and suggest the possibility of developing sensors exhibiting specific response to individual odors. In the case where such sensors are of the aforesaid type employing fluorescence emitting liposomes, it will become possible to secure sensors usable in the present invention by, for example, employing optical sensors to pick up the fluorescence intensity.

Figure 5:
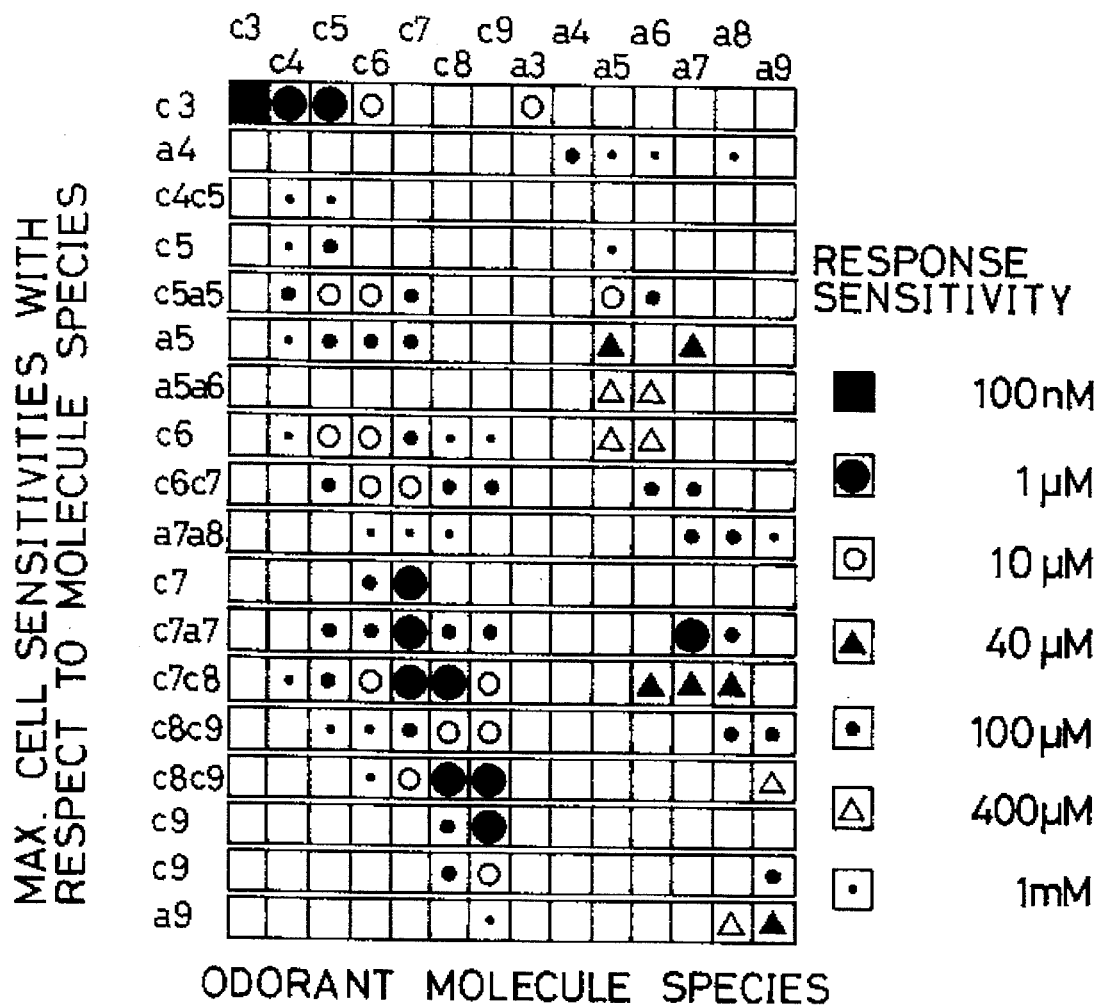
FIG. 5 is a chart showing examples of sensor materials capable of exhibiting specific response to different molecule species

It is known that the olfactory receptor cells (olfactory cells) that constitute the odor sensors of a living organism exhibit specific response with respect to low concentrations of a small number of odorant molecule species. FIG. 5 shows the response sensitivities of 18 olfactory cells (on the vertical axis) with respect to 14 odorant molecule species of similar molecular structure (horizontal axis). The sensitivity levels are roughly indicated by symbols in FIG. 5, while the specific names of the odorant molecule species c3–c9 and a3–a9 are shown at the bottom of the figure. Although no one has yet succeeded in directly building an artificial sensor with such characteristics, FIG. 5 at least discloses examples of materials for such sensors. On the other hand, since it is known, for example, that the resonant frequency of a crystal oscillator is changed by coating it with a specific combination of lipid membranes, it seems safe to say that the day is not far off when it will be possible to apply this technology to obtain specific sensors that exhibit characteristics with respect to odor like those in FIG. 5. Such sensors will of course also be usable in this invention.

Compared with the prior art, this invention shortens the time needed for measuring the component spectrum of chemical/physical quantities by a considerable margin (in some cases to a small fraction of the time previously required). This increased measurement speed opens up the possibility of achieving response speeds approaching or even exceeding those of living organisms. Moreover, the discrimination capability achieved is at least on a par with and in most cases superior to that of the prior art sensor systems developed. Owing to these features, the invention can be expected to be effectively applied in a wide range of engineering fields including, for example, technologies for the monitoring of production processes and technologies capable of imitating the functions of living organisms (such as robot sensors).

Japanese Pat. Application No. 5-354237 filed Dec. 27, 1993 is hereby incorporated by reference.

What is claimed is:

1. A method for discriminating a chemical/physical quantity comprising the steps of:

exposing at least one sensor array consisting of a plurality of sensor members exhibiting differing response ranges with respect to a chemical/physical quantity to be discriminated to stimulation and discriminating a stimulation component of the chemical/physical quantity from the order in which the sensor members produce lowest significant output levels.

2. A method according to claim 1, wherein a stimulation component of the chemical/physical quantity is discriminated not only from the order in which the sensor members produce lowest significant output levels but also from a difference in response characteristics between a sensor member which is first to produce a lowest significant output level and a sensor member which is second to produce a lowest output significant level.

3. A method according to claim 1, further comprising the steps of:

ascertaining an output rise rate during initial response of a sensor member which is first to produce a lowest significant output level and calculating a stimulation intensity of a stimulation component of the chemical/physical quantity from the output rise rate.

4. A method according to claim 1, wherein each sensor member consists of $m$ number ($m>1$) of like type sensors and the output level of each sensor member is defined as an output level obtained by comparing the sum of the output levels of the $m$ number of sensors with a value equal to $m$ times the output level produced by one sensor.

5. A method according to claim 1, further comprising the steps of:

disposing the sensor array in a measurement space or measurement vessel where the chemical/physical quantity to be discriminated is present and using an active agitation means to stir the chemical/physical quantity in the measurement space or the measurement vessel for ensuring uniform exposure of sensing surfaces of the sensor members of the sensor array thereto.

6. A method according to claim 1, further comprising the steps of:

disposing a reference sensor array configured identically with the sensor array in a stimulation-free space where it is not exposed to stimulation from the chemical/physical quantity, defining output levels of the sensor members of the reference sensor array as reference output levels under no stimulation, and using the reference output levels during discrimination of the chemical/physical quantity for correcting the output levels produced by the sensor members of the sensor array exposed to the stimulation.

7. A method according to claim 1, wherein the exposure of sensing surfaces of the sensor members of the sensor array is conducted by repeatedly alternating stimulation exposure periods and stimulation exposure rest periods.

8. A method according to claim 7, wherein the at least one sensor array is a plurality of sensor arrays disposed to be exposed to the same chemical/physical quantity, at least one of the plurality of sensor arrays is exposed to stimulation when at least one other thereof is in a stimulation exposure rest period, and the stimulation component of the chemical/physical quantity is discriminated on the basis of signals successively obtained in time series from a plurality of like type sensor members of the plurality of sensor arrays.

9. A method for discriminating a chemical/physical quantity comprising the steps of:

exposing at least one sensor array consisting of $n$ number of sensor members exhibiting differing response ranges with respect to a chemical/physical quantity to be discriminated to stimulation and discriminating a stimulation component of the chemical/physical quantity and a stimulation intensity of the stimulation component on the basis of response characteristics of the $n$ number of sensor members during their transient output level rise periods.

10. A method according to claim 9, wherein the stimulation component is discriminated from information regarding which sensor member is first to produce a lowest significant output level.

11. A method according to claim 10, wherein the stimulation component is discriminated on the basis of information regarding which sensor member is the first to produce a lowest significant output level and differences in transient output level rise period dynamic characteristics between a sensor member which is first to produce a lowest significant output level and sensor members which are second and later to produce a lowest output significant level.

12. A method according to claim 9, wherein the stimulation intensity is calculated on the basis of an output level rise rate of a sensor member which is first to produce a lowest significant output level.

13. A method according to claim 9, wherein each sensor member is constituted of $m$ number ($m>1$) of like type sensors and the output level of each sensor member is defined as an output level obtained by comparing the sum of the output levels of the $m$ number of sensors with a value equal to $m$ times the output level produced by one sensor.

14. A method according to claim 9, further comprising the steps of:

disposing the sensor array in a measurement space or measurement vessel where the chemical/physical quantity to be discriminated is present and using an active agitation means to stir the chemical/physical quantity in the measurement space or the measurement vessel for ensuring uniform exposure of sensing surfaces of the sensor members of the sensor array thereto.

15. A method according to claim 9, further comprising the steps of:

disposing a reference sensor array configured identically with the sensor array in a stimulation-free space where it is not exposed to stimulation from the chemical/physical quantity, defining output levels of the sensor members of the reference sensor array as reference output levels under no stimulation, and using the reference output levels during discrimination of the chemical/physical quantity for correcting the output levels produced by the sensor members of the sensor array exposed to the stimulation.

16. A method according to claim 9, wherein the exposure of sensing surfaces of the sensor members of the sensor array is conducted by repeatedly alternating stimulation exposure periods and stimulation exposure rest periods.

17. A method according to claim 16, wherein the at the least one sensor array is a plurality of sensor arrays disposed to be exposed to the same chemical/physical quantity, one of the plurality of sensor arrays is exposed to stimulation when another thereof is in a stimulation exposure rest period, and the stimulation component of the chemical/physical quantity is discriminated on the basis of signals successively obtained in time series from a plurality of like type sensor members of the plurality of sensor arrays.

18. An apparatus for discriminating a chemical/physical quantity comprising:

at least one sensor array consisting of a plurality of sensor members exhibiting differing response ranges with respect to a chemical/physical quantity, stimulation component identification circuit means for monitoring outputs of the plurality of sensor members and identifying a stimulation component of the chemical/physical quantity from the order in which the sensor members produce lowest significant output levels after exposure of the sensor array to the chemical/physical quantity, and stimulation intensity evaluation means for, based on a transient output level rise period dynamic characteristic of a sensor member which is first to produce a lowest significant output level after exposure to the chemical/physical quantity, calculating a stimulation intensity of a stimulation component in a range of the chemical/physical quantity corresponding to the sensor member concerned.

19. An apparatus according to claim 18, wherein not only the order in which the sensor members produce the lowest significant output levels but also differences in transient output level rise period dynamic characteristics between a sensor member which is first to produce a lowest significant output level and sensor members which are second and later to produce a lowest significant output level are used by the stimulation component identification means to identify a stimulation component in a range of the chemical/physical quantity corresponding to the sensor member which is first to produce a lowest significant output level.

20. An apparatus according to claim 19, wherein the stimulation component identification circuit means includes memory means for storing various combinations of said order of the sensor members and said differences in transient output level rise period dynamic characteristics between the sensor member which is first to produce a lowest significant output level and the sensor members which are second and later to produce a lowest significant output level and also storing, as standard combination patterns, known relationships between said various combinations and stimulation components of the chemical/physical quantity, the stimulation component identification circuit means determining one combination from among the various combinations by comparing with the standard combination patterns the combination of said order of the sensor members actually obtained as information from the sensor array and said differences in transient output level rise period dynamic characteristics between the sensor member which is first to produce a lowest significant output level and the sensor members which are second and later to produce a lowest significant output level, and identifying the stimulation component corresponding to the determined pattern as the detected stimulation component.

21. An apparatus according to claim 18, wherein the transient output level rise period dynamic characteristic used by the stimulation intensity evaluation means for calculating the stimulation intensity is the output level rise rate of the sensor member during its initial response period.

22. An apparatus according to claim 18, wherein each sensor member is constituted of $m$ number ($m>1$) of like type sensors disposed in close proximity and the output level of each sensor member is defined as an output level obtained by comparing the sum of the output levels of the $m$ number of sensors with a value equal to $m$ times the output level produced by one sensor.

23. An apparatus according to claim 18, further comprising a measurement space or measurement vessel in which the sensor array is disposed in the presence of the chemical/physical quantity and an active agitation means to stir the chemical/physical quantity in the measurement space or the measurement vessel for ensuring uniform exposure of sensing surfaces of the sensor members of the sensor array thereto.

24. An apparatus according to claim 18, further comprising a reference sensor array configured identically with the sensor array and disposed in a stimulation-free space where it is not exposed to stimulation from the chemical/physical quantity, the output levels of the sensor members of the reference sensor array being defined as reference output levels under no stimulation and the reference output levels being used during discrimination of the chemical/physical quantity for correcting the output levels produced by the sensor members of the sensor array exposed to the stimulation.

25. An apparatus according to claim 18, further comprising means for conducting the exposure of sensing surfaces of the sensor members of the sensor array by repeatedly alternating stimulation exposure periods and stimulation exposure rest periods.

26. An apparatus according to claim 25, wherein the at the least one sensor array is a plurality of sensor arrays disposed to be exposed to the same chemical/physical quantity, one of the plurality of sensor arrays is exposed to stimulation when another thereof is in a stimulation exposure rest period, and the identification of the stimulation component by the stimulation component identification circuit means and the calculation of the stimulation intensity of the stimulation component by the stimulation intensity evaluation means are conducted on the basis of signals successively obtained in time series from a plurality of like type sensor members of the plurality of sensor arrays.

27. An apparatus for discriminating a chemical/physical quantity comprising:

a plurality of apparatus units each having a sensor array consisting of a plurality of sensor members exhibiting differing response ranges with respect to a chemical/physical quantity, stimulation component identification circuit means for monitoring outputs of the plurality of sensor members and identifying a stimulation component of the chemical/physical quantity from the order in which the sensor members produce lowest significant output levels after exposure of the sensor array to the chemical/physical quantity, and stimulation intensity evaluation means for, based on a transient output level rise period dynamic characteristic of a sensor member which is first to produce a lowest significant output level after exposure to the chemical/physical quantity, calculating a stimulation intensity of a stimulation component in a range of the chemical/physical quantity corresponding to the sensor member concerned, the sensor arrays of the plurality of apparatus units being disposed to be exposed to the same chemical/physical quantity, the sensor array of one of the apparatus units being exposed to stimulation when the sensor array of another apparatus unit is in a stimulation exposure rest period, and the chemical/physical quantity being discriminated on the basis of stimulation component identification outputs successively obtained in time series from the stimulation component identification circuit means of the apparatus units and stimulation intensity outputs obtained in time series from the stimulation intensity evaluation means of the apparatus units.

* * * * *

UNITED STATES PATENT AND TRADEMARK OFFICE
CERTIFICATE OF CORRECTION

PATENT NO. : 5,541,851
DATED : July 30, 1996
INVENTOR(S) : Takaaki SATO, et al.

It is certified that error appears in the above-indentified patent and that said Letters Patent is hereby corrected as shown below:

On the title page, Item [73], the Assignee, should read:

--[73] Assignee: Agency of Industrial Science & Technology, Ministry of International Trade & Industry, Tokyo, Japan--

Signed and Sealed this

Fifth Day of November, 1996

Attest:

BRUCE LEHMAN

*Attesting Officer*  *Commissioner of Patents and Trademarks*